United States Patent [19]
Rondelet et al.

[11] Patent Number: 5,254,096
[45] Date of Patent: Oct. 19, 1993

[54] SYRINGE PUMP WITH GRAPHICAL DISPLAY OR ERROR CONDITIONS

[75] Inventors: Jean-Claude Rondelet, St. Etienne de Crossey; Jean-Michel Dupouy, La Tronche, both of France

[73] Assignee: Becton, Dickinson and Company, Franklin Lakes, N.J.

[21] Appl. No.: 950,385

[22] Filed: Sep. 23, 1992

[51] Int. Cl.⁵ .............................................. A61M 1/00
[52] U.S. Cl. ..................................... 604/152; 417/63
[58] Field of Search ................. 604/152, 151, 155; 417/63

[56] References Cited

U.S. PATENT DOCUMENTS

| | | | |
|---|---|---|---|
| 4,137,913 | 2/1979 | George | 604/152 |
| 4,396,385 | 8/1983 | Kelly et al. | 604/152 |
| 4,642,098 | 2/1987 | Lundquist | 604/152 |
| 4,985,015 | 1/1991 | Obermann et al. | 604/152 |
| 5,085,643 | 2/1992 | Larkin et al. | 604/152 |

*Primary Examiner*—John G. Weiss
*Attorney, Agent, or Firm*—Michael G. Schwarz

[57] ABSTRACT

A syringe pump is disclosed, having a housing, a motor driven pusher for pushing the plunger of a syringe and various transducers to determine error conditions in the placement of the syringe in the syringe pump, the pushing force of the pusher on the syringe and the engagement of the pusher drive mechanism. The syringe pump is provided with a clamp for holding the syringe in place and a device for preventing fluid from being siphoned out of the syringe. There is also a device for engaging and disengaging the motor drive mechanism. A position sensor senses the position of the syringe plunger in the barrel. A display graphically represents the syringe. Indicia are provided on the display to alert the user of conditions in the mechanism for holding the syringe in place, antisiphon device, the syringe drive engagement mechanism and the position of the plunger in the barrel.

11 Claims, 17 Drawing Sheets

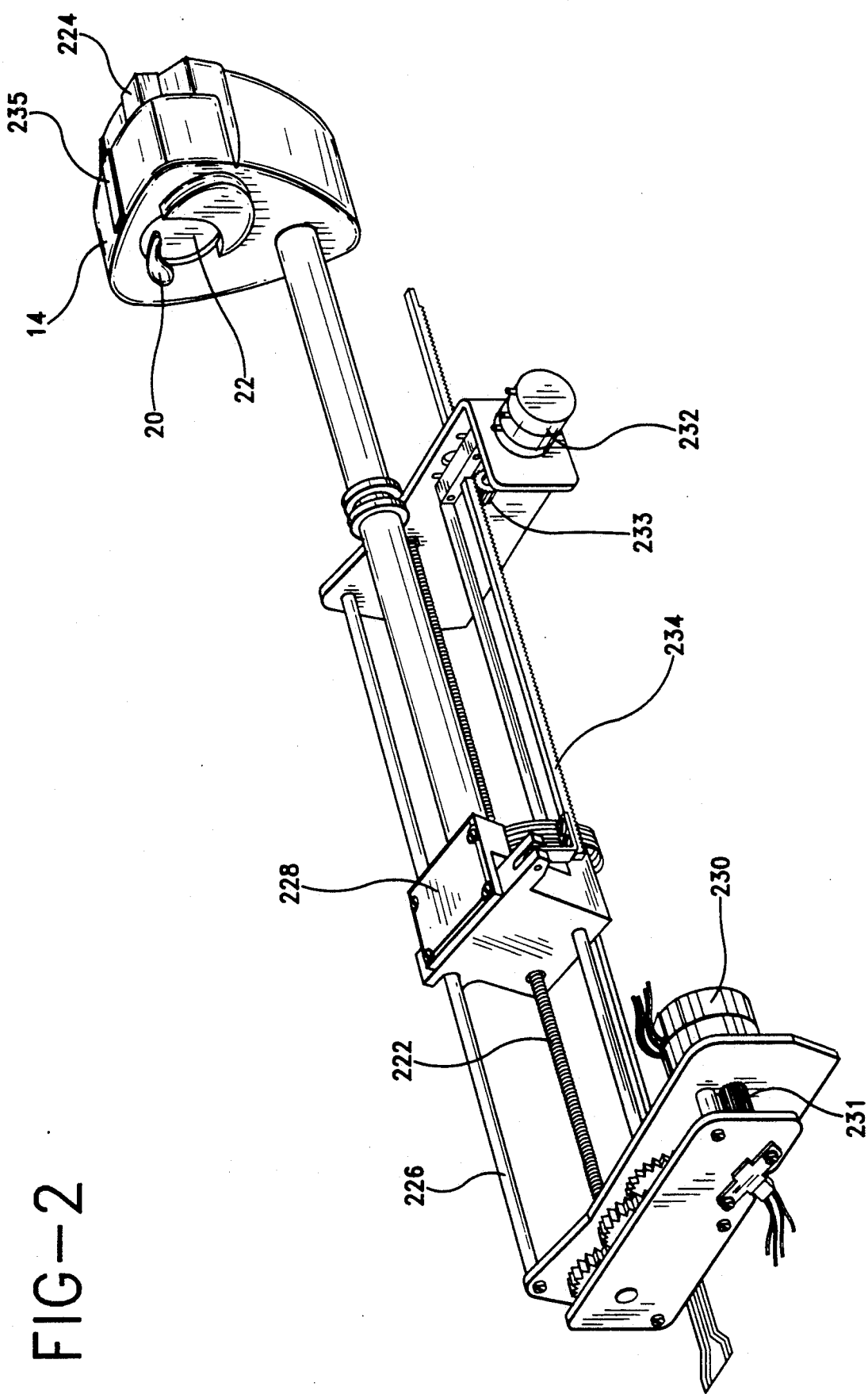

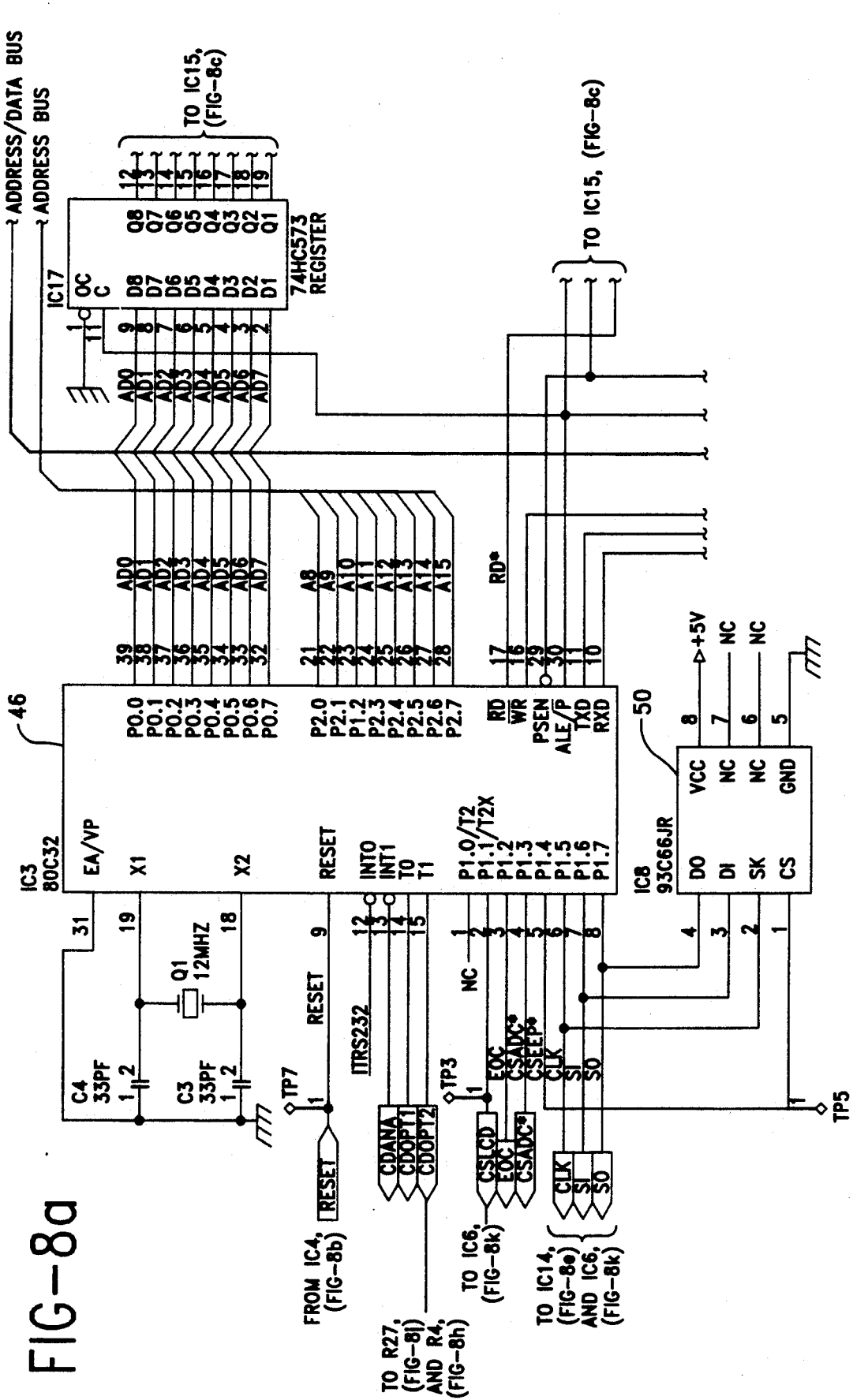

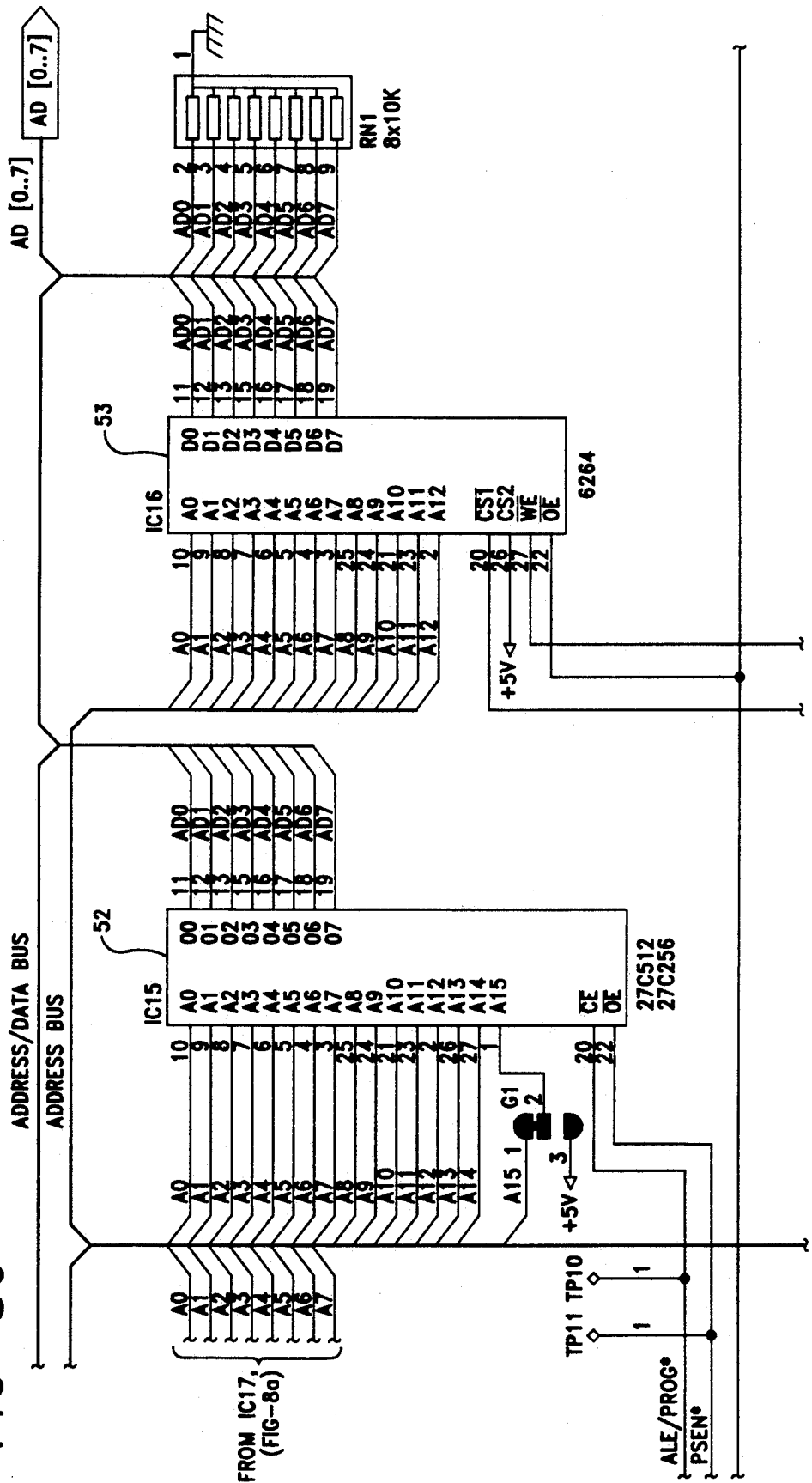

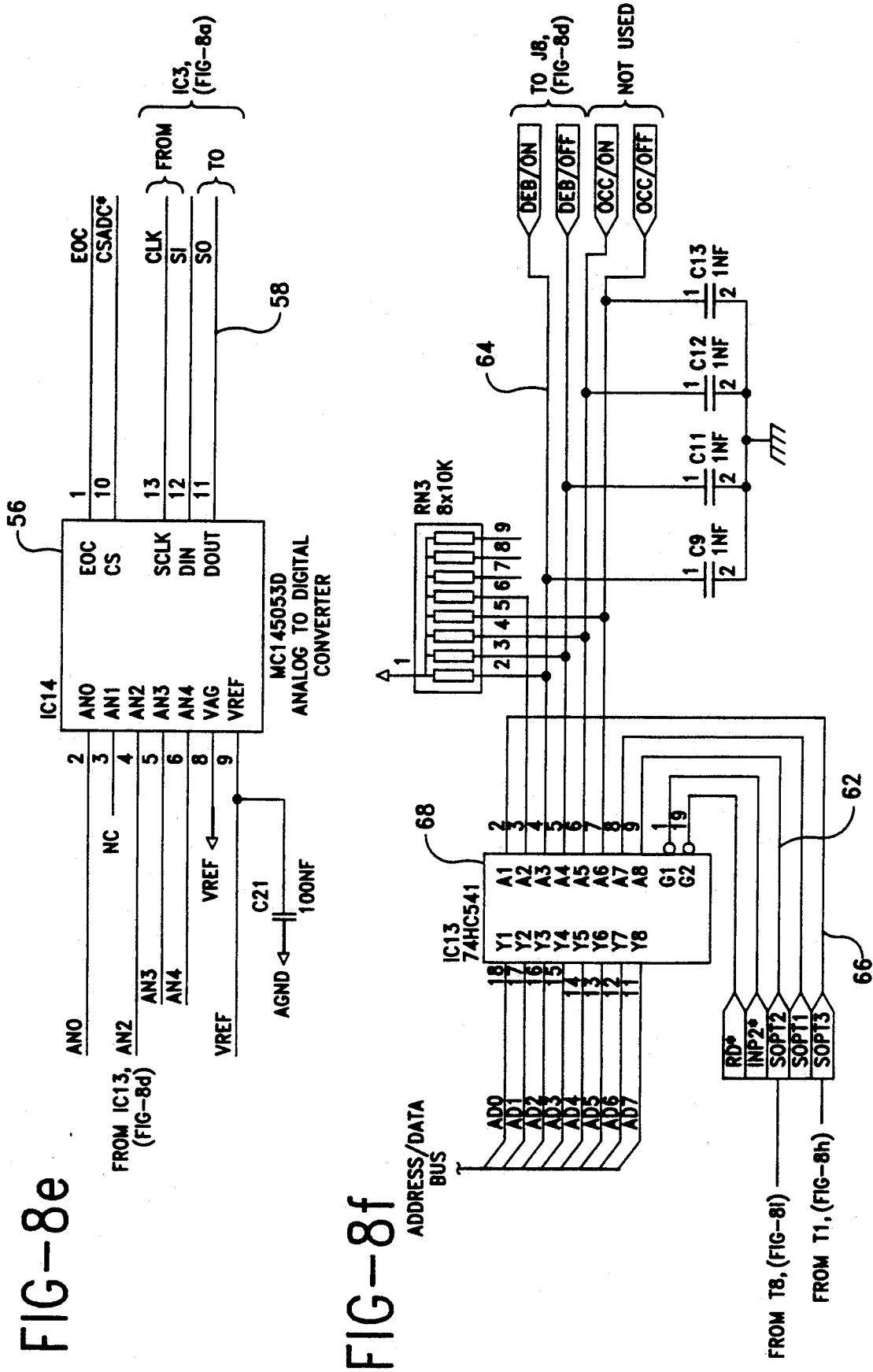

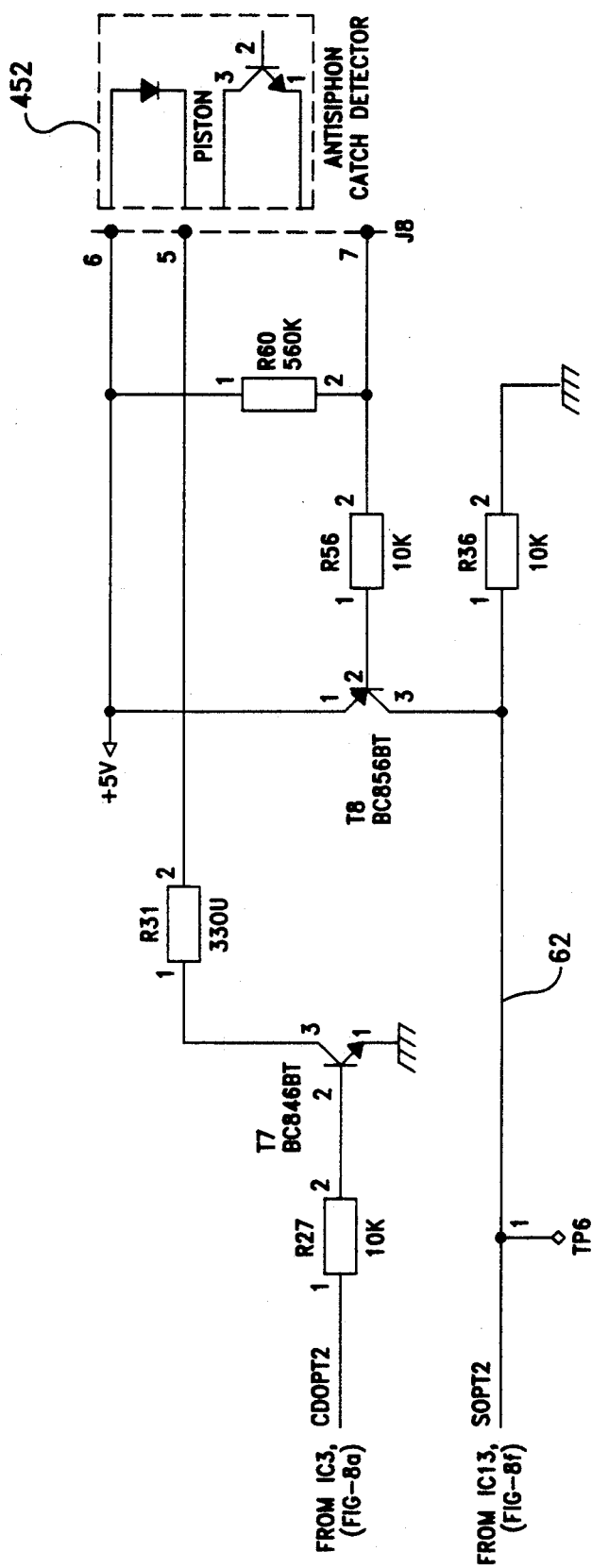

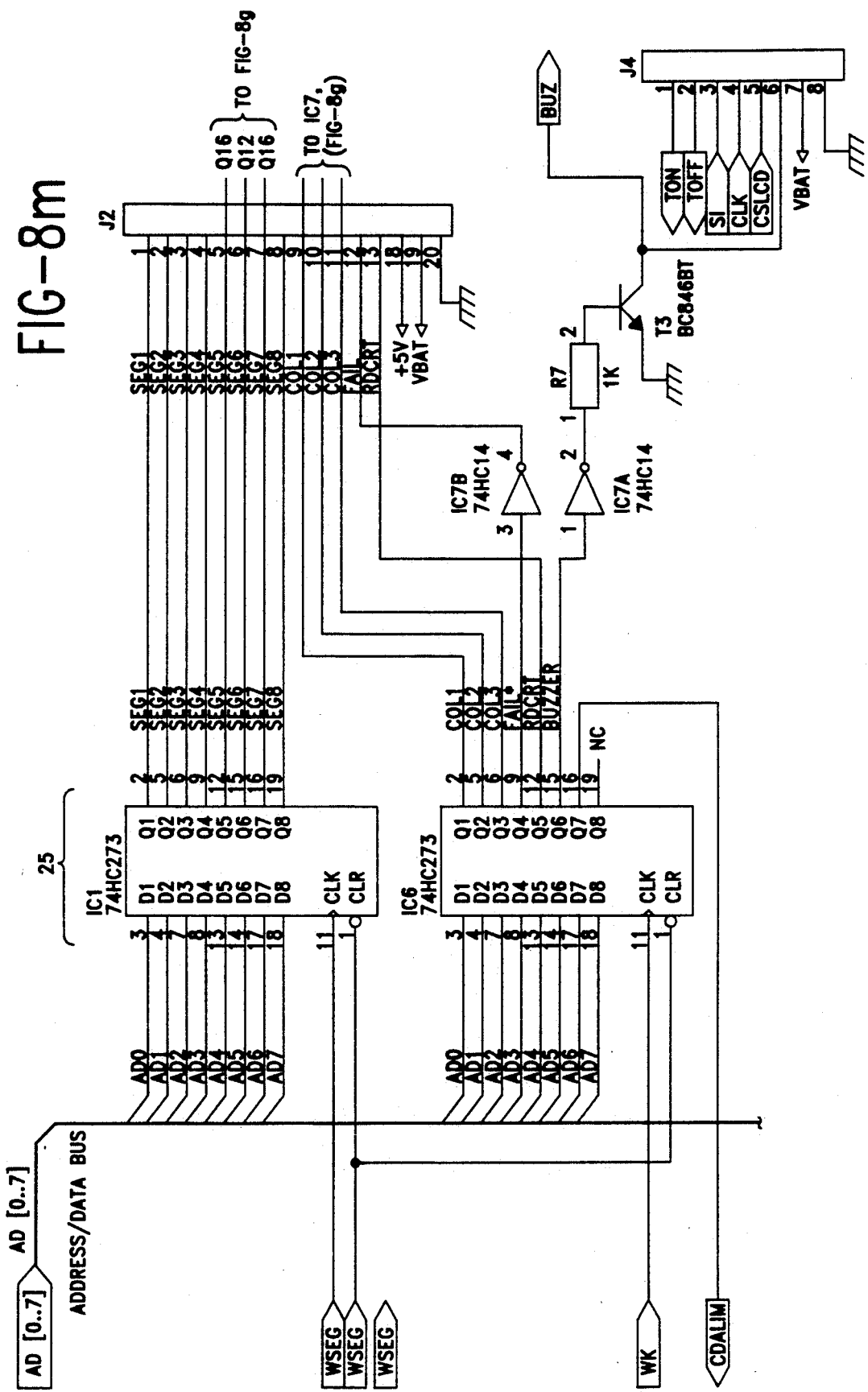

SYRINGE PUMP WITH GRAPHICAL DISPLAY OR ERROR CONDITIONS

BACKGROUND

1. Field of the Invention

This invention relates to the field of syringe pumps. In particular it relates to displays for indicating operating conditions in syringe pumps.

2. Background of the Invention

A syringe pump is a device for pumping fluid from a syringe into a patient. It typically comprises a housing to which a syringe is secured and a mechanism for pushing the plunger of the syringe to expel the fluid from the syringe, thus infusing the fluid into the patient. In the course of the operation of the syringe pump, certain conditions may arise at various parts of the pump. Using this invention, the user is informed of error conditions in the syringe pump by means of indicia on a display.

In prior art syringe pumps, the user has been informed of error conditions by means of messages displayed on the syringe pump control panel. These messages have been in the form of codes or flashing indicia. The applicants are unaware of any prior art syringe pump which has a single graphical representation of a syringe with indicia of all detected error conditions on that syringe and at points corresponding to the points at which the error conditions have arisen.

SUMMARY OF THE INVENTION

The invention is made up of a syringe pump having the following components: The syringe pump is housed in a housing which contains the drive mechanism for pushing the plunger of the syringe. The syringe is secured to the housing by means of a syringe clamp. In order to ensure that the syringe is securely held in place during the operation of the pump, the clamp is provided with a detector which detects the position of the clamp. The detector produces an electrical signal if the clamp is not properly positioned.

The pump also has a mechanism for holding the plunger in place so that it cannot move independently of the pusher, thus preventing fluid from being siphoned from the syringe. This antisiphon device is also provided with an electronic sensor which produces an electrical signal if the antisiphon device is not properly positioned.

The pusher is driven by means of a motor driven lead screw and a half nut which engages the lead screw. In order to facilitate the positioning of the pusher relative to the syringe, the half nut can be disengaged from the lead screw. A transducer is provided to detect whether or not the half nut is engaged with the lead screw. The pump also has a mechanism for detecting the position of the syringe plunger relative to the barrel. An indicium is activated when the plunger has fully entered the barrel.

The syringe pump has a display for alerting the user to error conditions arising at all or some of the points described above. The display is in the form of a graphical representation of a syringe. The graphical representation of the syringe has indicia located at the points on the graphical representation which generally correspond to the points on the actual syringe at which the error conditions described above may occur. Thus the display has indicia at all or some the following points: The point on the syringe barrel at which the clamp holds the barrel in place; the point on the plunger at which the antisiphon device engages the plunger; and the point on the plunger at which the plunger makes contact with the syringe pusher. When an error condition arises at any of the above identified points on the actual syringe, the corresponding indicium on the graphical representation will be activated.

The display also has an indicium at a position on the graphical representation corresponding to the point at which the stopper of the syringe plunger resides when the syringe plunger has fully entered the syringe barrel. When the plunger has fully entered the barrel of the syringe, the indicium will be activated.

Thus the user is provided with a simple, easy to read means for identifying the location of error conditions and the end of the infusion cycle in the syringe pump.

BRIEF DESCRIPTION OF THE DRAWINGS

FIG. 2 is a perspective view of the drive mechanism of the syringe pump;

FIG. 8a-m are schematic diagrams of the main electronic components of the invention.

DETAILED DESCRIPTION

Figure 1:
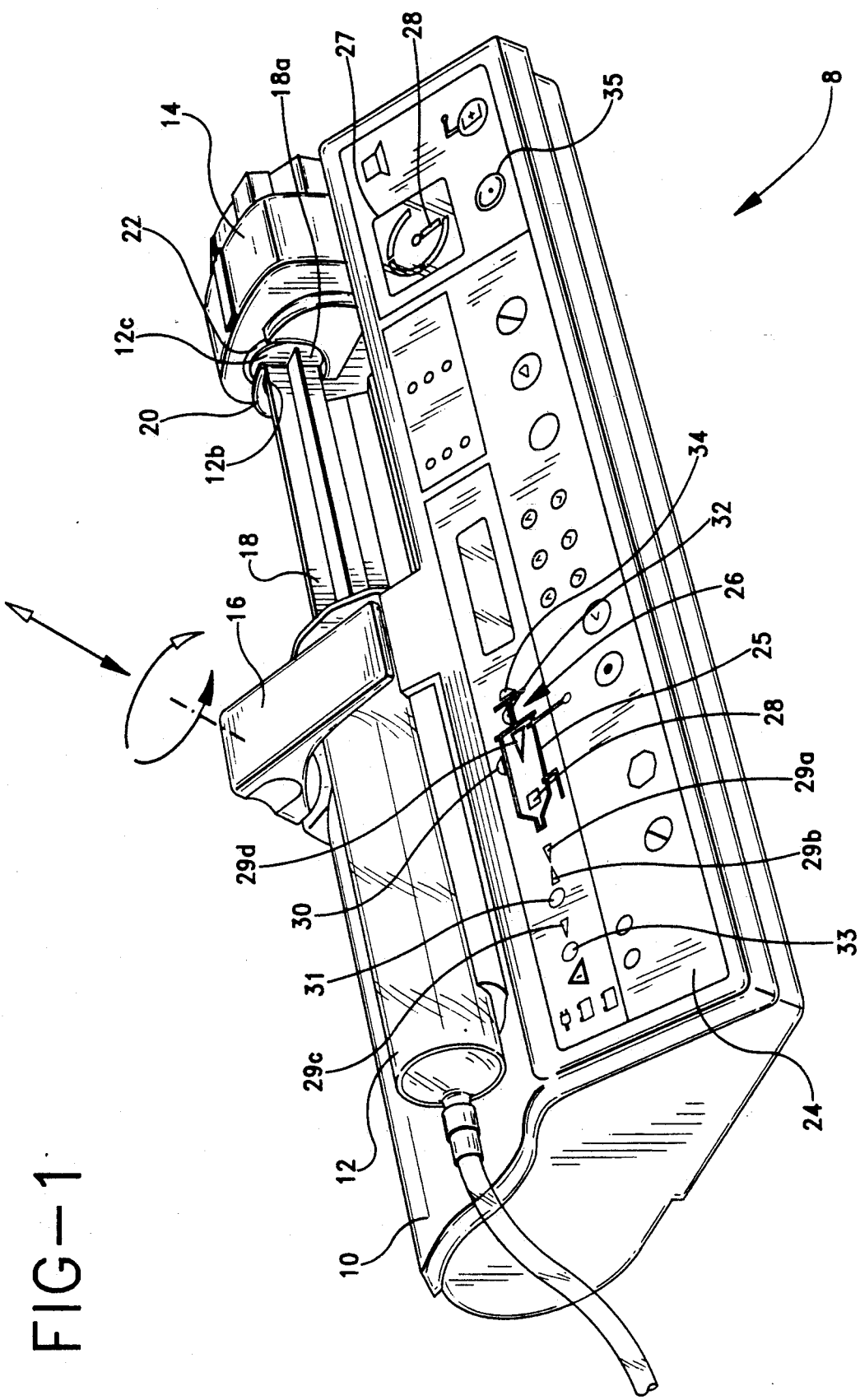
FIG. 1 is a perspective view of a syringe pump embodying the invention.

A syringe pump 8 embodying the invention is shown in FIG. 1. Housing 10 supports syringe barrel 12, pusher 14 and syringe clamp 16. Syringe clamp 16 holds syringe barrel 12 in place on housing 10. Plunger 18 is pushed by pusher 14 which is driven by an electric motor via a lead screw (see FIG. 2).

Pusher 14 is provided with antisiphon catch 20 which engages flange 18a of plunger 18, thus preventing plunger 18 from moving independently of pusher 14. Pusher 14 is also provided with pressure plate 22 for pushing directly against flange 18a thereby pumping fluid from syringe barrel 12.

Figure 3:
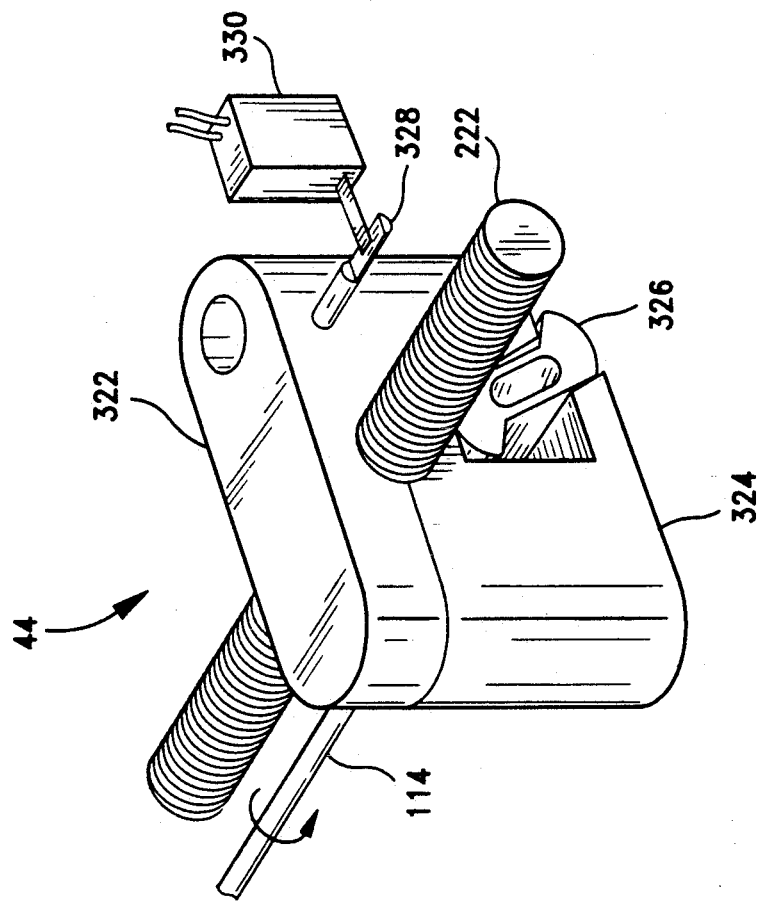
FIG. 3 is a perspective view of the lead screw and half nut mechanism inside pusher block of the syringe pump.
Figure 6:
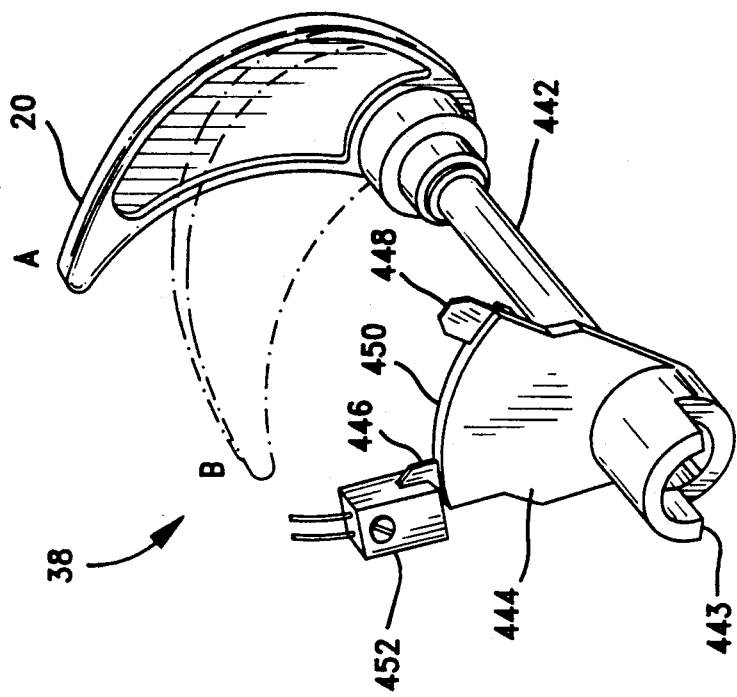
FIG. 6 is a perspective view of the antisiphon catch detector.

FIG. 2 shows the chassis and mechanical components of pump 8. Chassis 226 carries motor 230 and lead screw 222. Motor 230 drives lead screw 222 via gear assembly 232. Pusher 14 is driven by the interaction of pusher block 228 with lead screw 222. Pusher block contains half nuts 322, 324 which interact with lead screw 222 (see FIG. 3).

Pusher block 228 carries rack 234 such that rack 234 moves in unison with pusher block 228. Rack 234 is linked via pinion 233 to rotary potentiometer 232. Thus as pusher 14 pushes plunger 18, due to the movement of pusher block 228, the position of pusher block 228 and hence plunger 14 is sensed by rotary potentiometer 232. The output of rotary potentiometer 232 indicates the position of plunger 18. Rotary potentiometer 232 is a five turn rotary potentiometer of 1 Kohm impedance, 0.25 W power rating and a linearity better than 0.25% of full scale.

Display panel 24 contains controls for adjusting various parameters of the pump. Display panel 24 also contains graphic 26 which is a graphical representation of syringe barrel 12 and plunger 18. Graphic 26 is made up of an outline 25 of the syringe, showing the barrel and the plunger. Graphic 26 also includes indicia 30, 32 and 34. Also provided are end of infusion indicator 28, flow direction arrows 29a, 29c and 29d and occlusion indicator 29b. Indicium 30 is located at a point on graphic 26 corresponding to the point on syringe barrel 12 at which clamp 16 holds syringe barrel 12 in place. Indicium 32 is located at a point on graphic 26 which corresponds to the point on plunger 18 at which antisiphon catch 20 makes contact with plunger 18. Indicium 34 is located at a point on the graphic which corresponds to the point at which pusher 14 pushes flange 18a of plunger 18, i.e. pressure plate 22.

Indicia 30, 32 and 34 are linked via electronics which will be described herein to transducers respectively connected to syringe clamp 16, antisiphon catch 20 and half nut 332. Thus, when an error condition is detected at any one of the aforementioned, the corresponding indicium will indicate the error condition on graphic 26. End of infusion indicator 28 is linked to rotary potentiometer 232. When plunger 18 has fully entered syringe barrel 12, indicium 28 will be activated to indicate the end of the infusion cycle.

End of infusion indicator 28 is at a position on graphic 26 corresponding to the position of syringe plunger 18 when the end of the infusion is reached. Direction arrows 29a, 29c and 29d represent the flow of the infusate from syringe barrel 12. Occlusion indicator 29b points in the direction of the force resulting from the occurrence of an occlusion in the delivery line.

Figure 7:
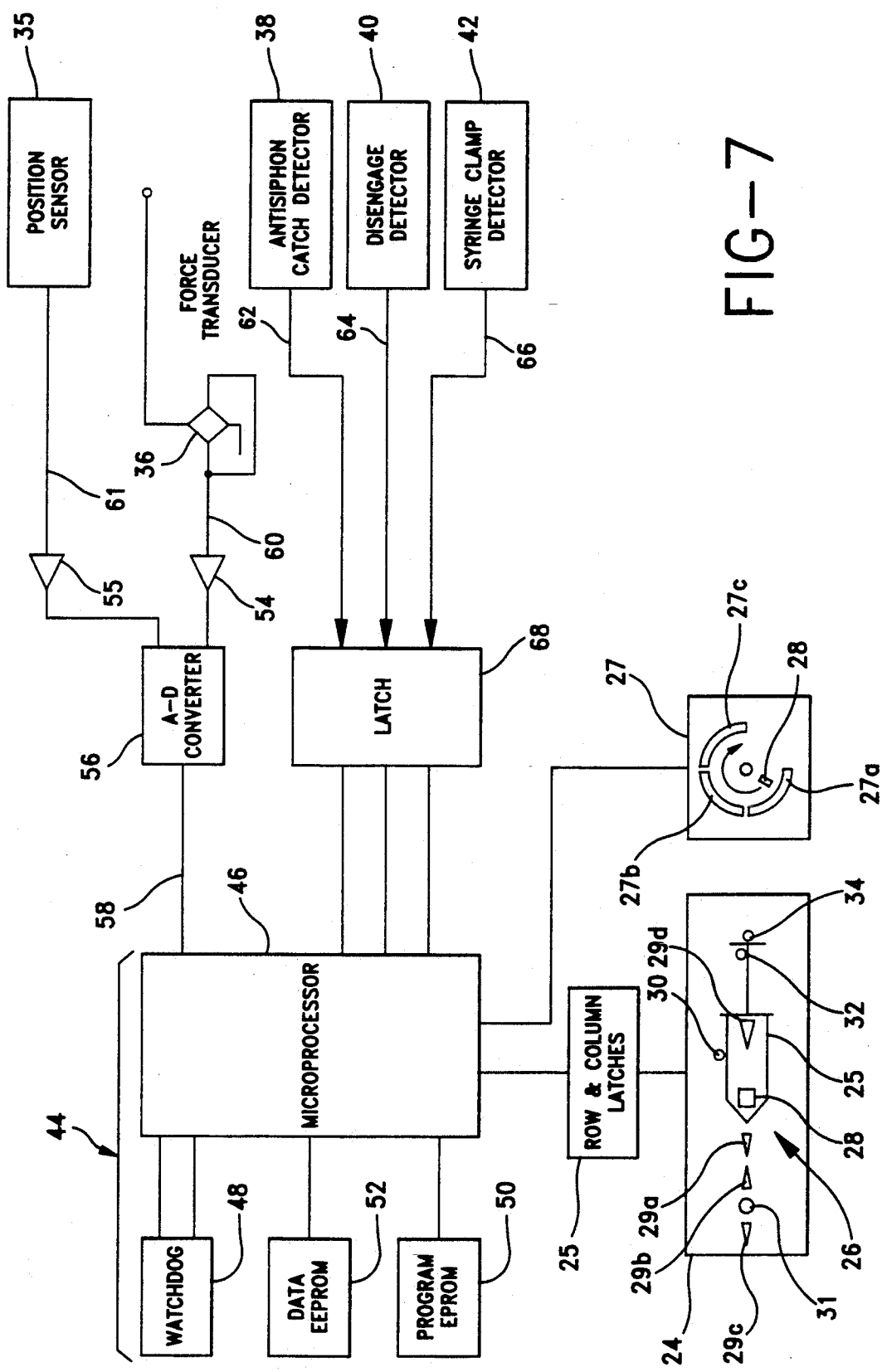
FIG. 7 is a block diagram of the electronic components of the invention.

FIG. 7 is a block diagram showing the main electronic components of the invention. Five transducers are provided to detect the parameters of the syringe pump which are displayed. The transducers are: position sensor 35, force transducer 36, antisiphon catch detector 38, disengage detector 40 and syringe clamp detector 42. The outputs of these transducers 62, 64 and 66 respectively are fed into central processing unit 44 via various signal processing or latching modules which will be described in detail herein.

Schematic diagrams of the various modules are shown in FIGS. 8a-n. The values and types of the components are indicated on the schematic diagrams.

Figure 8B:
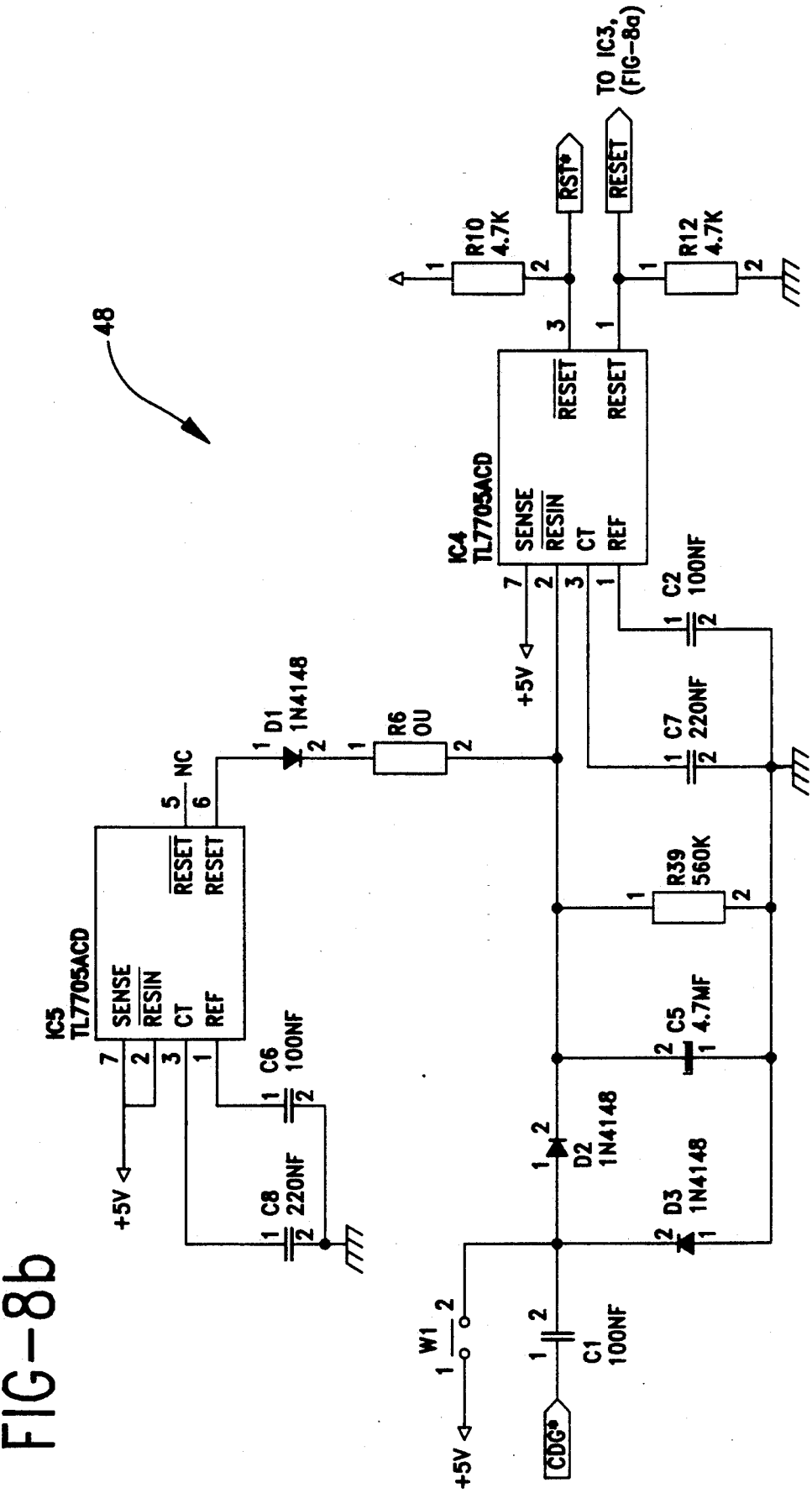

Central processing unit 44 comprises microprocessor 46 (FIG. 8a) with random access memory 53 (FIG. 8a), watchdog 48 (FIG. 8b), EPROM 50 (FIG. 8a) and EEPROM 52 (FIG. 8c). Watchdog 48 monitors microprocessor 46 to ensure its proper operation. EEPROM 52 contains data concerning the parameters of each of the various types of syringes which may be used in the pump, such as brand, size and model of syringe, volume of syringe, number of motor steps per ml infused, "hardheight" (i.e. the distance from the plunger flange to the open end of syringe barrel when the plunger has fully entered the barrel, the syringe frictional force in gF (i.e. Ff) and the syringe pressure under a 5 kg load in millibars (i.e. Pc). EPROM 50 contains a software program which controls the operation of the syringe pump.

Figure 8D:
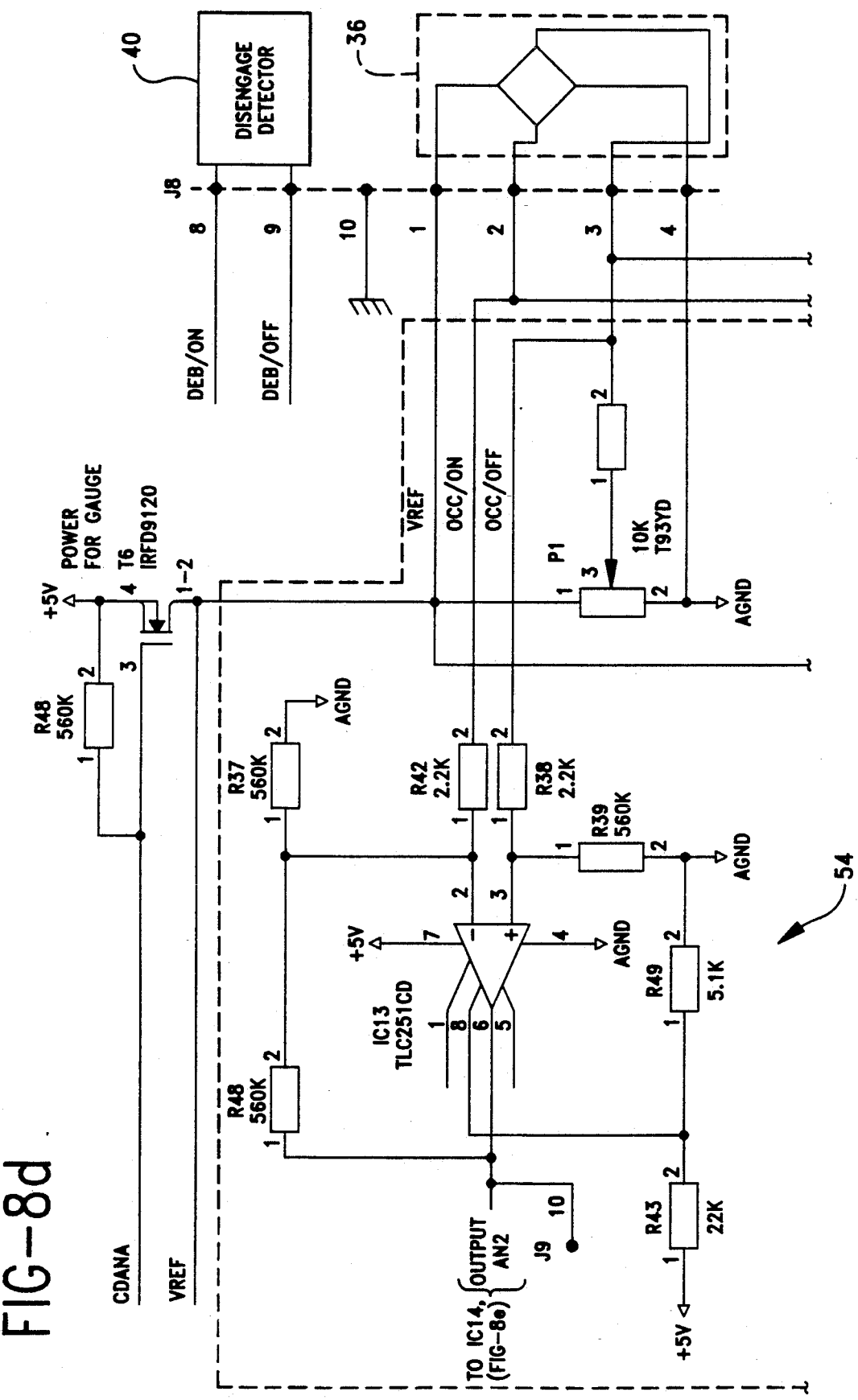

The output of force transducer 36 is conditioned by signal conditioning circuit 54 (FIG. 8d), which converts the output of force transducer 36 into a form suitable for input into analog to digital converter 56 (FIG. 8e). Output 61 of position sensor 35 is conditioned by signal conditioning circuit 55 and is then also fed into analog to digital converter 56. Analog to digital converter 56 digitizes the analog outputs 60 and 61 and produces serial output 58 which is in turn fed into input port 60 of microprocessor 46.

EEPROM 52 contains data representing the outputs of position sensor (i.e. "hard height" of the syringe) corresponding to the points at which plunger 18 has fully entered syringe barrel 12 for various types of syringe.

Figure 8G:
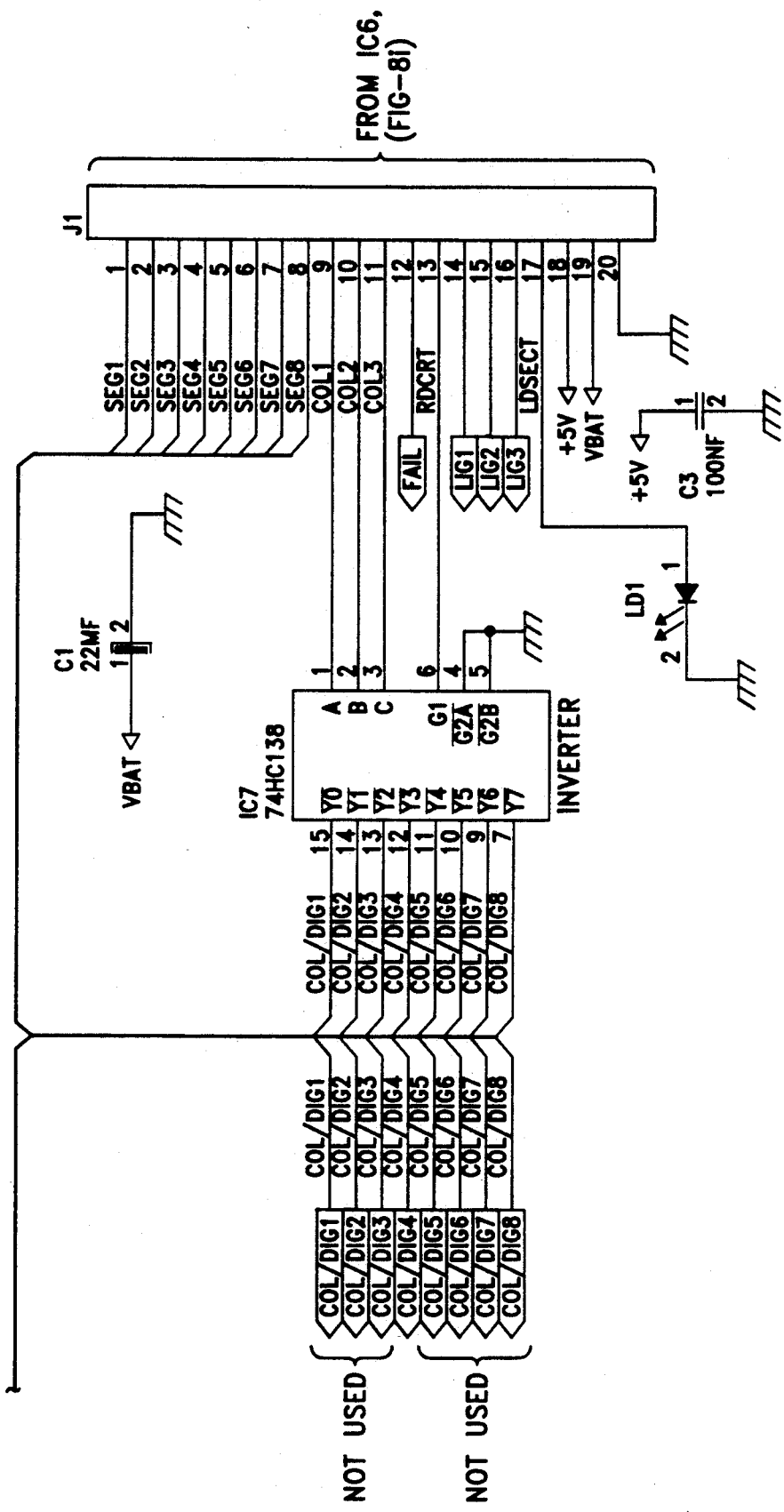
Figure 8H:
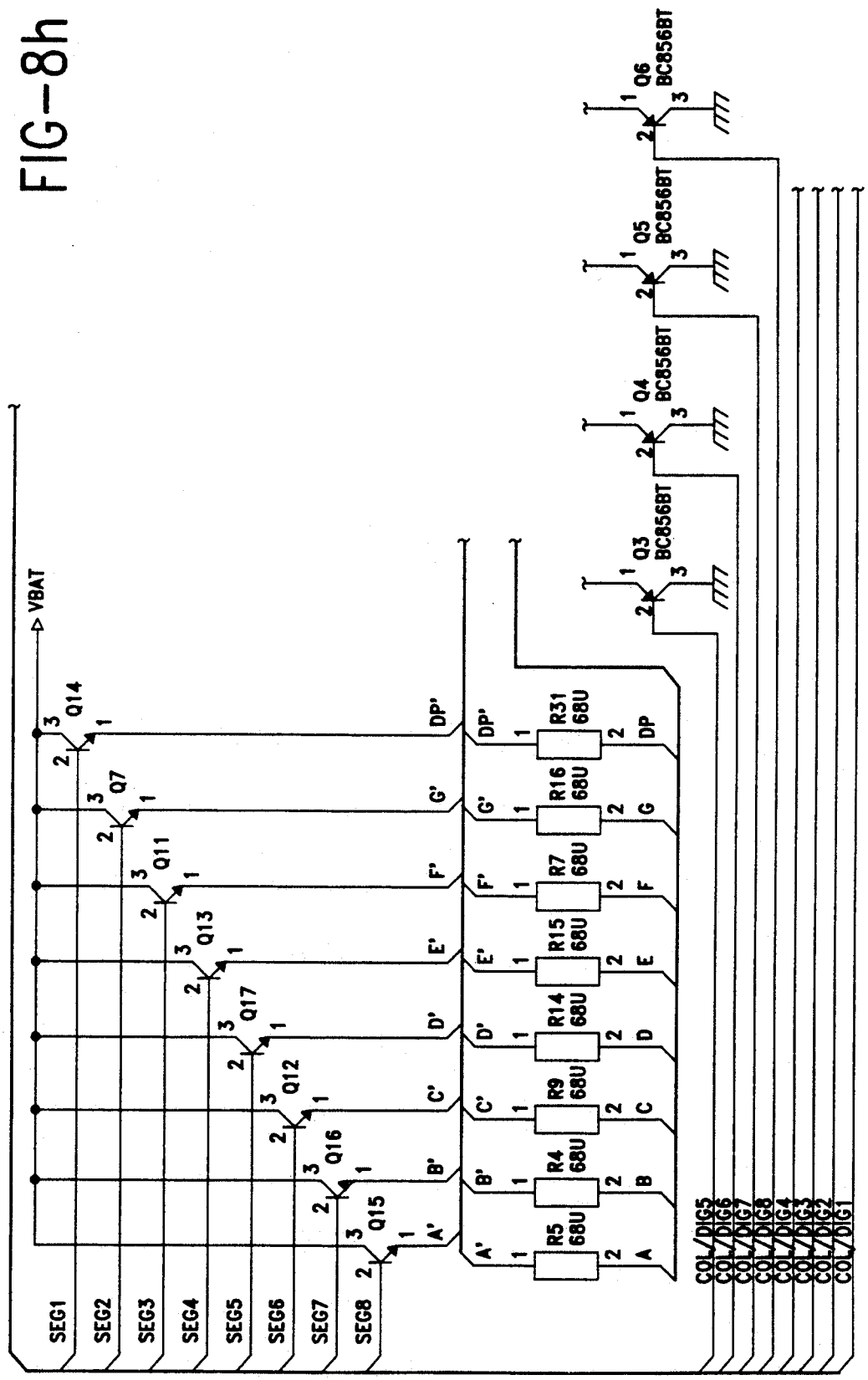
Figure 8I:
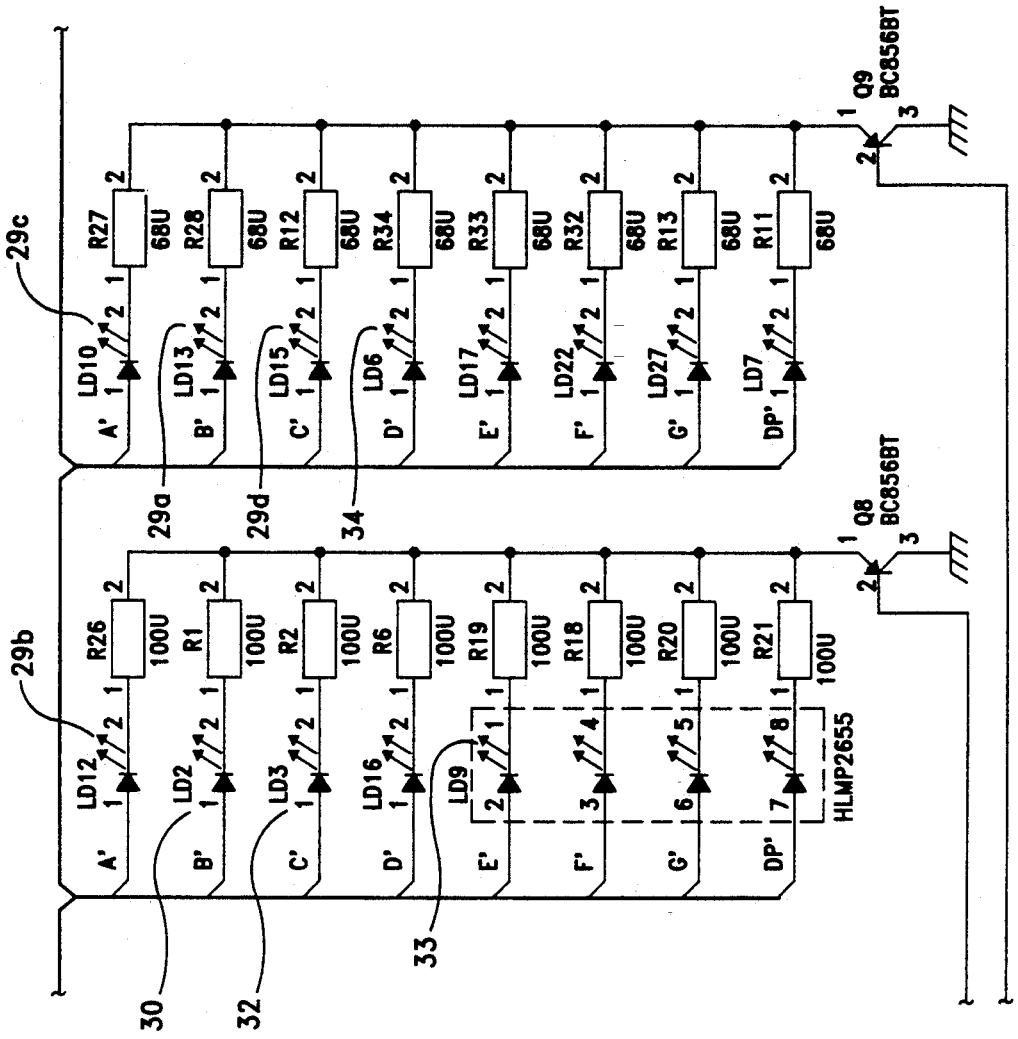

When antisiphon catch 20 is disengaged, antisiphon catch detector 38 produces digital output 62 (See FIG. 8i). Similarly the opening of disengage mechanism 44 causes disengage detector 40 to produce an output 64 (FIG. 8f) and the opening of syringe clamp 16 causes syringe clamp detector (FIG. 8h) to produce an output 66. Each output 62, 64, 66 is fed into central processing unit 44 via latch 68 (FIG. 8f).

Microprocessor 46 causes error conditions at clamp 16, disengage mechanism and antisiphon catch 20 to be displayed on display panel 24 (FIG. 8g). Display panel 24 comprises graphical representation 26 which in turn comprises syringe outline 28, indicium 30 indicating an error condition at syringe clamp 16, indicium 32 which indicates an error condition at antisiphon catch 20 and indicium 34 which indicates that disengage 44 mechanism is disengaged.

Figure 8J:
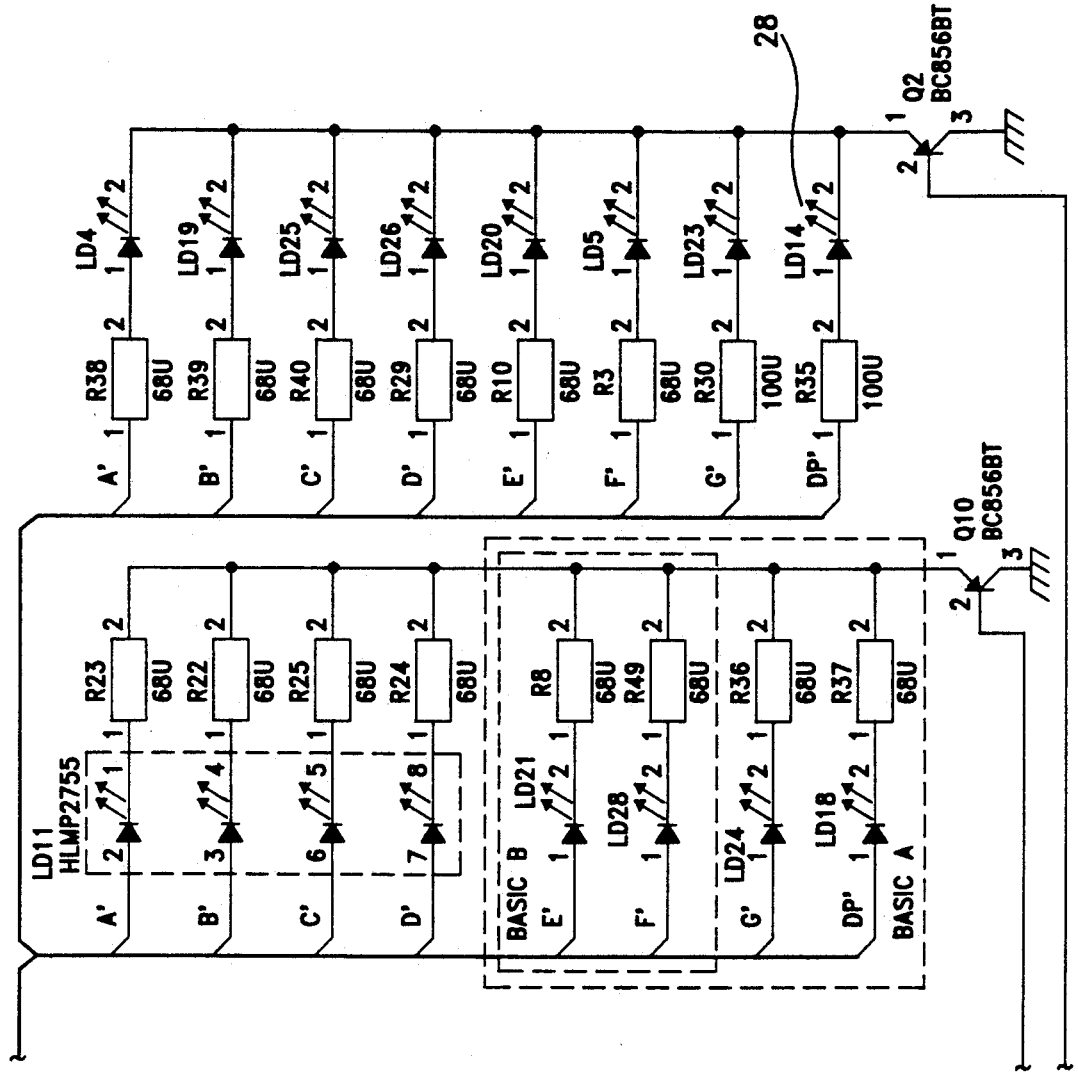
Figure 8K:
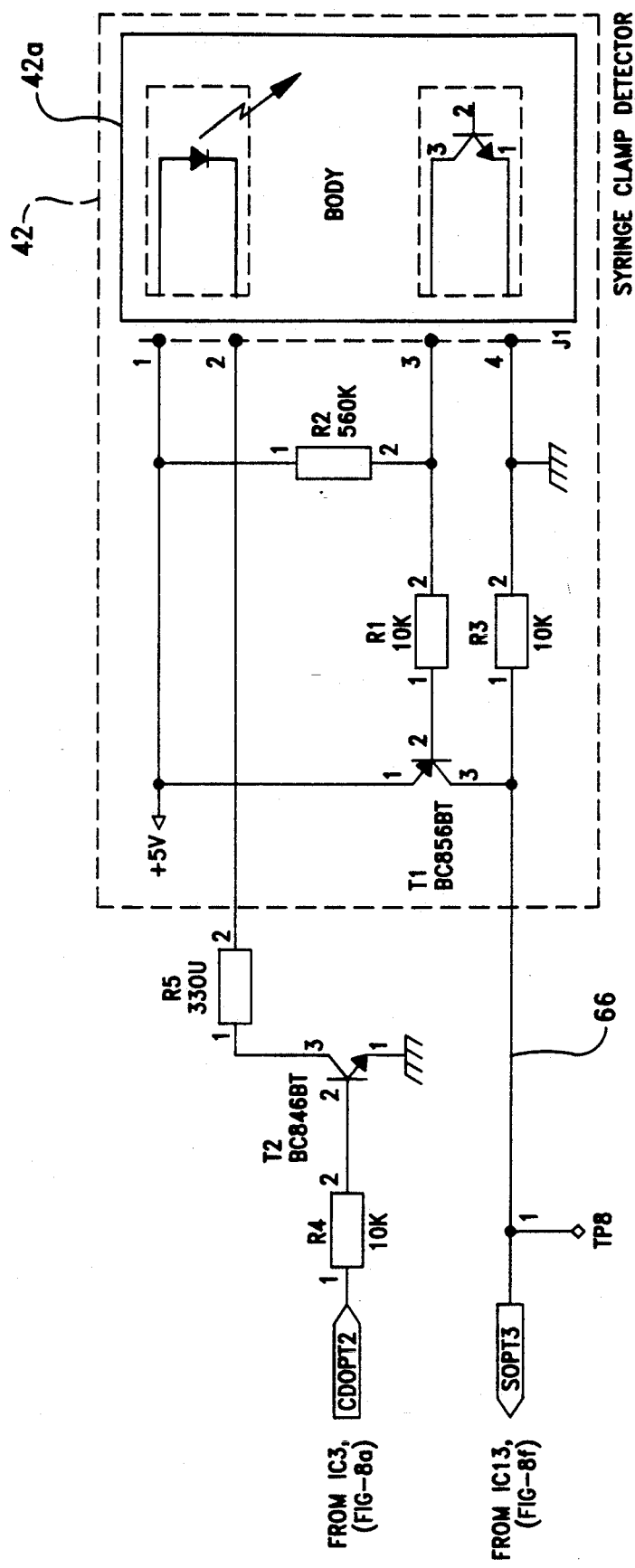

In FIG. 8j, indicia 30, 32 and 34 correspond to light emitting diodes LD2, LD3 and LD16 respectively. Indicia 30, 32 and 34 are activated under the control of microprocessor 46 when error conditions arise. Indicia 30, 32 and 34 are driven through row and column latches 25 (IC1 and IC6 in FIG. 8m) which in turn activate appropriate driver transistors (FIG. 8g). LD2, LD3 and LD16 are part of a matrix of light emitting diodes which are lit up when the row and column of the matrix corresponding to the position of the particularly light emitting diode are activated. The remaining light emitting diodes in the matrix (not shown) are not used in the invention. For simplicity, the full matrix is not shown. The other diodes in the matrix which are not shown light up other indicia on the panel of syringe pump which are not material to the invention.

Figure 5:
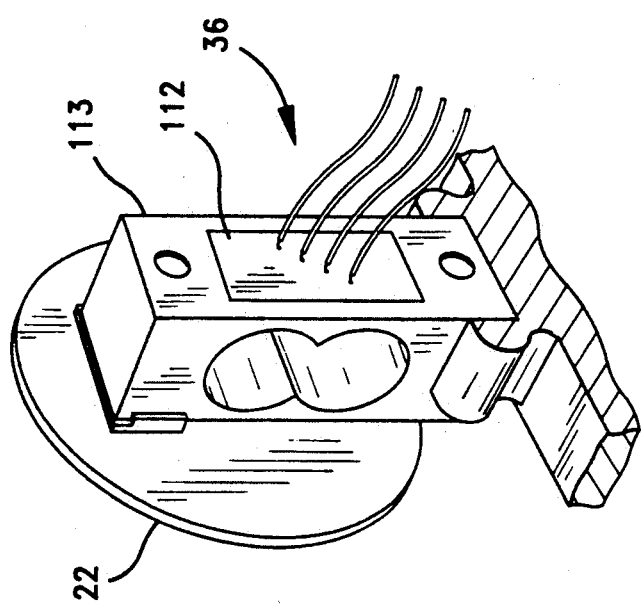
FIG. 5 is a perspective view of the pusher disc and force transducer.

FIGS. 5 shows force transducer 36 in greater detail. Force transducer 36 is made up of four strain gauges in a wheatstone bridge configuration. The bridge has an impedance of 350 ohms or 1 Kohm with a tolerance of ±15%. The range of force measurements is 0 to 150N. The bridge sensitivity is 1.7 mV/V to 2.4 mV/V under a load of 150N at 20 degrees centigrade. The bridge is powered intermittently under the control of microprocessor 46 (line CDANA in FIGS. 8a and 8d) in order to conserve energy.

Strain gauges 112 are glued onto beam 114. When force is applied to pressure plate 22, beam 114 flexes, causing strain gauges 112 to distort and produce output 60.

Output 60 of force transducer 36 is fed into conditioning module 54 (FIG. 8d) and thereafter into analog to digital converter 56 which converts the conditioned output into serial output 58. Serial output 58 is then fed into input 60 of microprocessor 46.

The output 61 of position sensor 35 is similarly conditioned by signal conditioning circuit 55 and fed into analog to digital converter 56.

Resident in EPROM 50 is a software program for microprocessor 46 which calculates the pressure inside syringe 12 continuously as the force on the plunger 18 is measured by force transducer 36. Certain parameters which are used by the program to calculate the pressure in the syringe and stored in EEPROM 52. Since syringe pump 8 is programmable to accommodate various types of syringe, a set of parameters for each type of syringe, is stored in EPROM 52.

The parameters stored in EEPROM 52 include:

Ff=average frictional force between the syringe plunger and the syringe barrel at null (atmospheric) pressure.

Pc=the pressure in the syringe when a calibration force is applied to the plunger. The calibration force is typically 5 kgF which leads to a value of Pc around 0.7 bar, a usual threshold for infusion pumps.

Fc=the force with which the plunger is loaded to obtain a pressure of Pc in the syringe.

The program in EPROM 50 is used by microprocessor 46 to calculate the pressure in the syringe. Microprocessor 46 then compares the calculated pressure with the pressure threshold selected by the user. If the calculated pressure exceeds the threshold, an occlusion alarm is generated by microprocessor 46.

The algorithm for calculating the pressure in the syringe is:

$$P = \frac{(F - Ff)}{Fc - Ff} \cdot Pc$$

where F is the force measured by force transducer 36 and Fc, Ff and Pc are the parameters defined above.

The main advantages of this formula over the traditional formula described in the BACKGROUND section above are (1) it is not highly dependent on the frictional force in the syringe which is known to vary with pressure and (2) that the cross sectional area of the syringe need not be determined. Rather, the pressure in the syringe is calculated using parameters which are easy to determine empirically.

The position of plunger 18 as detected by position sensor 35 is read by microprocessor 46 and compared with the "hard height" stored in EEPROM 52 for the particular type of syringe being used. If the position detected is the same as the hard height, microprocessor 46 actuates indicium 28 (LD14 in FIG. 8j, driven by transistors Q14 and Q2 in FIG. 8h).

Clamp 16 comprises a spring loaded shaft which enables clamp 16 to be lifted and turned so that the syringe can be placed and removed. Clamp 16 is provided with a syringe clamp detector 42 (FIG. 8h) which detects whether or not clamp 16 is properly placed. When clamp 16 is properly placed, output 66 is low. Detector 42 comprises optical detector 42a, and associated circuitry. Detector 42 is powered by a sampled power supply controlled by CPU 46.

Figure 4:
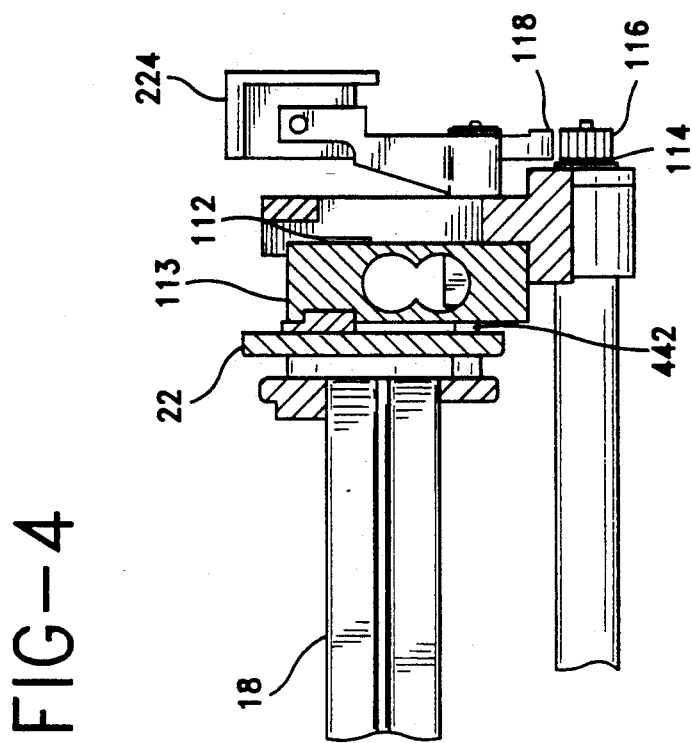
FIG. 4 is a cross sectional view of the pusher mechanism of the invention.

Disengage mechanism 44 (FIG. 3) comprises half nuts 322, 324 which interact with lead screw 222 so that pusher block 228 which holds half nuts 322, 324 (FIG. 2) may be separated by the rotation of cam 326. Cam 326 may be rotated by pressing lever 224 (see FIGS. 2 and 4) which in turn rotates shaft 114 and thus cam 326. Half nut 322 is provided with projection 328, which is linked to disengage detector switch 330.

When lever 224 is pressed, thus disengaging half nuts 322, 324, disengage detector switch 330 is activated. As long as half nut 322 is disengaged from lead screw 222, disengage detector switch 330 will be activated, causing output 64 to be high.

FIG. 7 shows antisiphon catch detector 38 in detail. Antisiphon catch 20 is attached to shaft 442 which is in turn linked to lever 234 (FIG. 2) via cam 444 so that antisiphon catch 20 can be disengaged. Also attached to shaft 442 is tab 444. Tab 444 moves in concert with antisiphon catch 20. Tab 444 is provided with ears 446 and 448 spaced apart by space 450. Detector 452 is an optical detector available from Optek Technology, Inc. of Carrollton, Tex. under part number OPB860 or OPB870. When antisiphon catch is correctly positioned on plunger 18, detector 452 is aligned with space 450 and is inactive. When antisiphon catch is improperly placed, i.e. is in either position A or position B, ears 446 or 448 interrupt the light beam in detector 452 and detector is activated and produces output 62. The electronics of disengage detector are shown in FIG. 8l.

Outputs 62, 64 and 66 are sequentially latched to microprocessor 46 by latch 68 (FIG. 8f). The latching of outputs 62, 64 and 66 provides a power saving since 36, 38, 40, 42 need only be powered while they are monitored. The sampled power supply and latching of outputs 62, 64 and 66 are controlled by microprocessor 46 by means of a program stored in EPROM 50. The precise details of how this is accomplished are not material to this invention.

When the microprocessor detects that any one of outputs 60, 62, 64 has gone high, it generates a signal to activate the corresponding indicium on display panel 24. Thus, when output 62 (the antisiphon catch detector output) goes high, indicium 32 is activated, when output 64 (the disengage detector output) goes high, indicium 34 is activated and when output 66 (the syringe clamp detector output) goes high, indicium 34 is activated. The user is thus alerted of an error condition at any one of antisiphon catch 20, syringe clamp 16 or disengage mechanism 44 by means of a display showing the location on the syringe at which the error condition occurs.

We claim:

1. A syringe pump for pumping fluid from a syringe having a barrel and a plunger, the plunger having a flange, the syringe pump comprising:

a housing;

a pusher for pushing the plunger;

clamp means for engaging the syringe barrel and for holding the syringe barrel in a stationary position relative to the housing;

clamp detector means for detecting whether or not the syringe is properly held in position relative to the housing by the clamp means and for producing an output indicative of whether the syringe is properly held in position relative to the housing;

antisiphon means for engaging the plunger and holding the plunger stationary relative to the pusher, thereby preventing the plunger from moving independently of the pusher;

antisiphon detector means for detecting whether the plunger is properly engaged by the antisiphon means and for producing an output indicative of whether the plunger is properly engaged by the antisiphon means;

a display comprising a graphical representation of the syringe, the graphical representation comprising a representation of the syringe barrel and the plunger, first indicium means for indicating the output of the clamp detector means and located at a point on the display generally corresponding to the position on the syringe barrel where the clamp engages the syringe barrel and second indicium means for indicating the output of antisiphon detector means, and located at a point on the display generally corresponding to the position on the plunger where the antisiphon means engages the plunger;

electronic circuitry for transmitting the outputs of the clamp detector means and the antisiphon detector means respectively to the first and second indicia means such that the display indicates whether or not the syringe is properly held relative to the housing and whether or not the plunger is properly engaged by the antisiphon means.

2. The syringe pump of claim 1 further comprising:

drive means for driving the pusher;

disengage means for engaging and disengaging the drive means;

disengage detector means for detecting whether the drive means is engaged or disengaged and for producing an output indicative of whether the drive means is engaged or disengaged, wherein the display further comprises a third indicium means for indicating the output of the disengage detector means, such that the third indicium means is positioned on the graphical representation of the syringe corresponding to the syringe plunger; and, wherein the electronic circuitry further comprises means for transmitting the output of the third detector means to the third indicium means.

3. The syringe pump of claim 1 wherein the plunger comprises a stopper and further comprising means for determining whether the plunger has fully entered the barrel and wherein the display comprises a fourth indicium for indicating whether the plunger has fully entered the barrel, the fourth indicium corresponding to the point in the barrel at which the stopper of the plunger is located when the plunger has fully entered the barrel.

4. The syringe pump of claim 1 wherein the electronic circuitry comprises a microprocessor.

5. The syringe pump of claim 2 wherein the third indicium means is located adjacent a point on the display generally corresponding to the back of the flange of the plunger.

6. The syringe pump of claim 1 wherein the first indicium means is activated when the syringe is not properly held in position on the housing by the clamp means.

7. The syringe pump of claim 1 wherein the second indicium means is activated when the plunger is not properly engaged by the antisiphon means.

8. The syringe pump of claim 2 wherein the third indicium is activated when the drive means is disengaged.

9. The syringe pump of claim 2 wherein the drive means comprises a lead screw and a half nut, the half nut engaging the lead screw when the drive means is engaged.

10. The syringe pump of claim 7 wherein the third indicium means lights up when the half nut does not engage the lead screw.

11. The syringe pump of claim 3 wherein the fourth indicium is activated when the plunger has fully entered the barrel.

* * * * *